United States Patent [19]

Devonald et al.

[11] Patent Number: 5,275,924
[45] Date of Patent: Jan. 4, 1994

[54] AMPHIPHILIC COMPOUNDS FOR SEQUENTIAL MONOLAYER DEPOSITION

[75] Inventors: David P. Devonald, Oldham; Michael G. Hutchings, Bury; Timothy G. Ryan, Great Ayton, all of England

[73] Assignee: Imperial Chemical Industries PLC, London, England

[21] Appl. No.: 754,013

[22] Filed: Sep. 3, 1991

[30] Foreign Application Priority Data

Sep. 5, 1990 [GB] United Kingdom ............... 9019365

[51] Int. Cl.$^5$ ............................................. G03L 1/73
[52] U.S. Cl. ................................. 430/495; 430/321; 430/945; 430/4; 252/582; 359/321
[58] Field of Search ............... 430/495, 321, 283, 4, 430/945; 252/582; 359/321

[56] References Cited

U.S. PATENT DOCUMENTS

| | | | |
|---|---|---|---|
| 4,327,020 | 4/1982 | Sasaki et al. | 534/689 |
| 4,783,151 | 11/1988 | Choe | 350/356 |
| 4,794,045 | 12/1988 | Robin et al. | 428/411.1 |
| 4,946,949 | 8/1990 | Wolf et al. | 534/885 |
| 4,970,120 | 11/1990 | Laschewsky et al. | 428/411.1 |
| 4,978,732 | 12/1990 | Wehrmann et al. | 528/71 |
| 5,009,815 | 4/1991 | Wakita et al. | 252/582 |
| 5,019,451 | 5/1991 | Lando | 428/411.1 |
| 5,053,168 | 10/1991 | Man et al. | 252/587 |

OTHER PUBLICATIONS

Stepanov et al., Optica Acta, vol. 31 No. 12 pp. 1335-1343, (1984).
Lovelock et al., J. Colloid and Interface Sci., vol. 108 No. 2 pp. 297-303, (Dec. 1985).
Mumby et al., Macromolecules, 19, 1054-1059, (1986).

*Primary Examiner*—Charles L. Bowers, Jr.
*Assistant Examiner*—John A. McPherson
*Attorney, Agent, or Firm*—Cushman, Darby & Cushman

[57] ABSTRACT

Amphiphilic compounds and oligomers and polymers derived therefrom suitable for Langmuir Blodgett deposition wherein the compounds have a polyamide backbone and hydrophobic groups pendant therefrom which pendant groups preferably contain chromophore groups. The compounds can be used to form non-centrosymmetric bilayers and are useful for forming various non-linear optical elements.

9 Claims, No Drawings

AMPHIPHILIC COMPOUNDS FOR SEQUENTIAL MONOLAYER DEPOSITION

This invention relates to a novel class of amphiphilic compounds which are particularly useful, although not exclusively so, in forming optical elements for use in optical devices with non-linear optical (NLO) properties.

The compounds of the present invention are suitable for applications that exploit second order non-linear optical properties, particularly the linear electro-optic effect. The size of the change is related to the first molecular hyperpolarisability, $\beta$, of the chromophore through both the size of $\beta$ and the degree of molecular ordering. The size of the molecular hyperpolarisability is determined by the structure of the molecule, but materials having large values of $\beta$ are ineffective if the structure of the material is symmetrically ordered rendering it non-polar.

Materials currently commercially exploited in devices because of their NLO properties include potassium dihydrogen phosphate (KDP), lithium niobate ($LiNbO_3$) and Group III/V semiconductor materials such as GaAs.

Certain organic materials have larger values of $\beta$ and various methods have been found for incorporating organic molecules into non-centrosymmetric structures. These methods include crystal growth techniques, multilayer Langmuir-Blodgett film deposition and the use of strong electric DC fields to pole NLO active chromophores grafted to polymer backbone.

The Langmuir-Blodgett technique (hereinafter termed LB technique) provides a number of advantages for fabrication of multilayer films for NLO devices. Firstly a relatively high degree of molecular order can be achieved compared to, for example, that produced by electric field poling. When conditions are optimised the NLO active species can be aligned parallel to each other.

Secondly, films of precise thickness can be produced in which the composition can be controlled at the molecular level.

The compounds of the present invention are particularly suitable for organising molecules into highly ordered arrays usign the LB technique, being transferable in ordered form to a substrate in a highly reproducible and efficient manner.

Accordin to the invention there are provided amphiphilic compounds and oligomers and polymers derived therefrom having the general formula

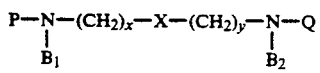

where X is selected from

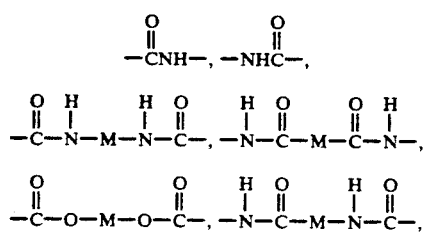

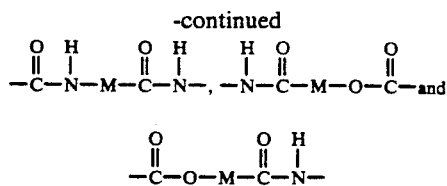

where M is a molecular moiety. x and y may be the same or different and are between 1 and 6, preferably 2 or 3, $B_1$ and $B_2$ may be the same or different and are chosen from phenyl, alkylphenyl or any molecular moiety made hydrophobic by attachment of a group containing from 8 to 40, preferably 10 to 20, carbon atoms. P is selected from a $C_1$ to $C_6$ alkyl group, preferably methyl,

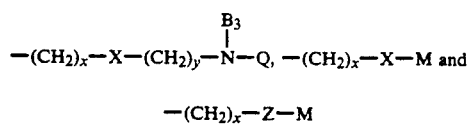

Q is selected from a $C_1$ to $C_6$ alkyl group, preferably methyl

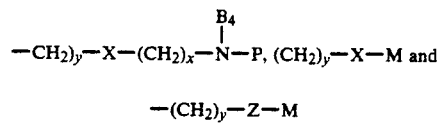

where Z is either

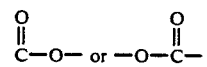

where $B_3$ and $B_4$ may be the same or different from $B_1$ and $B_2$ and are chosen from the same list of substituent groups with the proviso that when the compound contains only 2 nitrogen atoms in the chain both $B_1$ and $B_2$ must be molecular moieties made hydrophobic by attachment of a group containing 8 to 40 carbon atoms and when the compound contains only 3 nitrogen atoms at least one of $B_1$, $B_2$, $B_3$ or $B_4$ must be a molecular moiety made hydrophobic by attachment of a group containing 8 to 40 carbon atoms.

The groups $B_1$, $B_2$, $B_3$ and $B_4$ pendant to the polyamide backbone are chosen to provide specific properties. When the amphiphilic compound is to have NLO properties at least some of the moieties made hydrophobic by attachment of a group containing 8 to 40 carbon atoms should additionally contain a chromophore group. The nature of the chromophore group can be chosen to vary the linear optical properties, such as refractive index.

In order to obtain a film with non-linear optical properties containing stable bilayers with non-centrosymmetric order two classes of compound. I and II are provided with the general formula:

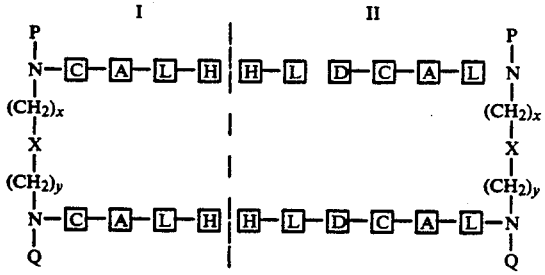

In compounds I and II the NLO chromophore is understood to be any organic moiety known to exhibit non-linear optical properties. In general the NLO molecule comprises a conjugated system (C) of π-bonds, substituted at or near one end by one or more π-electron acceptor groups (A) and at or near the other by a π-electron donor group (D). The donor and acceptor groups are preferably but not exclusively conjugated with the linking π-conjugated system. The π-conjugated system is to be taken as one of the following; aromatic ring systems (eg benzene), condensed aromatic ring systems (eg naphthalene), (poly)ene system (one or more conjugated π-bonds), (poly)yne system (one or more conjugated acetylene bonds), quinomethide systems, any of the above substituted by one or more heteratom replacement(s) of a carbon atom(s) (eg thiophene, furan, pyridine, pyrrole), and/or by one or more heteroatom replacement(s) of a C=C double bond(s) and combinations of the above with or without heteroatom replacement(s). The π-conjugated system can be optionally substituted. Such optional substitution may form a carbocyclic or heterocyclic ring, condensed or appended to the π-conjugated system. Specific examples of π-conjugating systems, C, are:

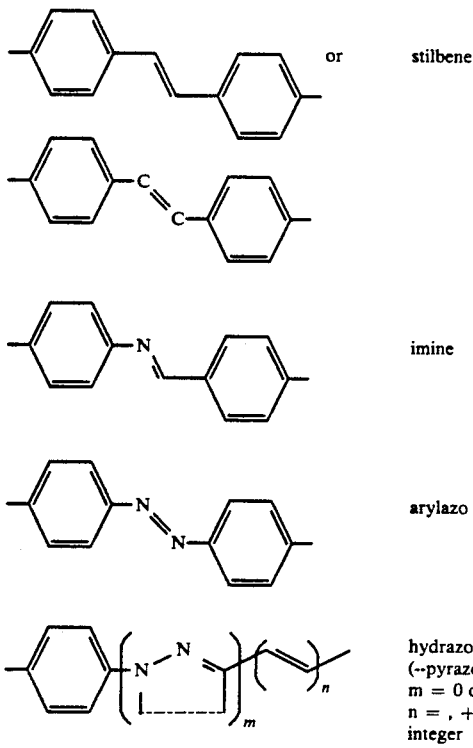

stilbene imine arylazo hydrazone (--pyrazoline)
m = 0 or 1
n = , +ve integer

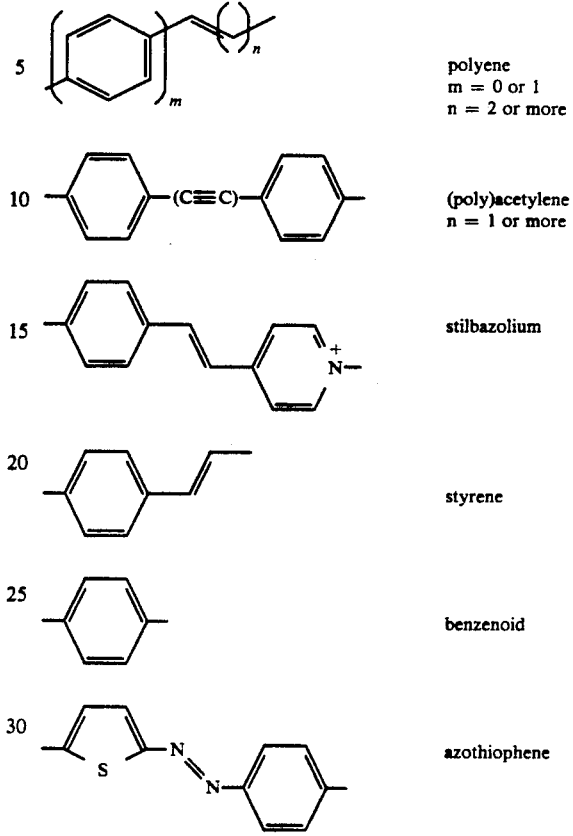

polyene
m = 0 or 1
n = 2 or more (poly)acetylene
n = 1 or more stilbazolium styrene benzenoid azothiophene The π-electron donor substituent(s), D, appended to the π-conjugated system are to be taken preferably, but not exclusively, from the following: amino, $NR_1R^2$; thio, $SR^1$; oxy, $OR^1$; phosphino, $PR^1R^2$, where $R^1$ and $R^2$ are organic substituents selected from: alkyl, cycloalkyl, aryl, heteroaryl, alkenyl, cycloalkenyl, alkynyl, any of which may be optionally substituted and contain heteroatom replacements.

For compound I the preferred donor is contained within the polyamide backbone and is preferably $NR^1R^2$.

The π-electron acceptor substituent(s), A, may be selected preferably but not exclusively from the following; nitro, $NO_2$; cyano, CN; nitroso, NO; ester, $CO_2R$; amide, $CONR^1R^2$; ketone, $COR^1$; formyl, COH; sulphone, $SO_2R^1$; sulphoxide, $SOR^1$; sulphonate ester, $SO_3R^1$; sulphonamide, $SO_2NR^1R^2$; phosphonate, $P(=O)OR^1OR^2$; phosphine oxide, $P(=O)R^1R^2$: boronate ester, $B(OR^1)OR^2$; N—pyridinium and substituted variants, and other positively charged quaternary salts. Also to be taken as suitable acceptor groups are heteroatoms especially N, when replacing carbon in an aromatic ring of the conjugated system, and more especially also quaternised versions of the same (eg stilbazolium). $R^1$ and $R^2$ are organic moieties as outlined above.

The hydrophobe H is a group containing 8 to 40 carbon atoms such as a long chain aliphatic group, preferably alkyl, alkenyl or cycloalkyl or a group containing a mixture of these. The carbon chain may be interrupted by heteroatoms, especially oxygen or sulphur. The carbon chain may be terminated with a functional group and may carry non-hydrophilic substituents such as halogen atoms, but is preferably a hydrocarbon. The group H is attached either directly to the conjugated system or via R₁ and/or R₂ or the acceptor group or donor groups.

The proportion of groups $B_1$, $B_2$, $B_3$ and $B_4$ (hereinafter termed groups B) that are functionalised with a hydrophobe having 8–40 carbon atoms can be less than 100%, but preferably 50% or more are provided with a hydrophobe. The distribution of hydrophobes can be precisely defined along the polyamide backbone to give alternating or block or random sequences.

A range of possible functional groups can be included in the hydrophobe to enable chemical cross-linking at the hydrophobe-hydrophobe interface.

For compounds I and II the NLO chromophore is attached to the polyamide backbone and to the hydrophobe by means of one or more linking groups selected from the following; direct bond, (poly)methylene, (poly)arylene, (poly)oxymethylene or (poly)oxypropylene chain. These are optionally substituted by appendage of one or more substituent(s), and/or by heteroatom replacement (eg ether, ester linkages). The attachment can be to the π-conjugated system of the NLO chromophore, or can be via substituents $R^1$ and $R^2$ attached to the π-electron acceptor group(s), (A), or the π-electron donor group(s), (D) above. In the case of attachment via π-donor groups, convenient substituents are dialkylamino, alkyl amino, alkylthio, alkoxy, ester, amide. In the case of π-acceptor groups, convenient substituents are ester, $-CO_2R^1$; amide, $-CONR^1R^2$; sulphonamide, $-SO_2NR^1R^2$; sulphonate ester, $-SO_3R^1$; sulphone, $-SO_2R^1$; sulphoxide, $-SOR^1$; ketone, $-COR^1$; boronate ester, $-B(OR^1)(OR^2)$; phosphine oxide, $-P(=O)R^1R^2$ The structure of a typical compound I is shown below.

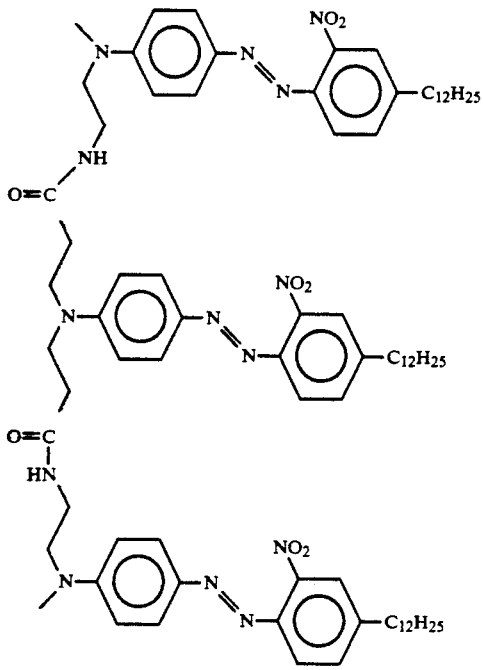

In the case of the compound II of a non-centrosymmetric bilayer the donor in the polyamide backbone can not be used as part of the NLO chromophore. Instead the chromophore can be linked via a linking group L as described above to the polyamide backbone. The structure below is an example.

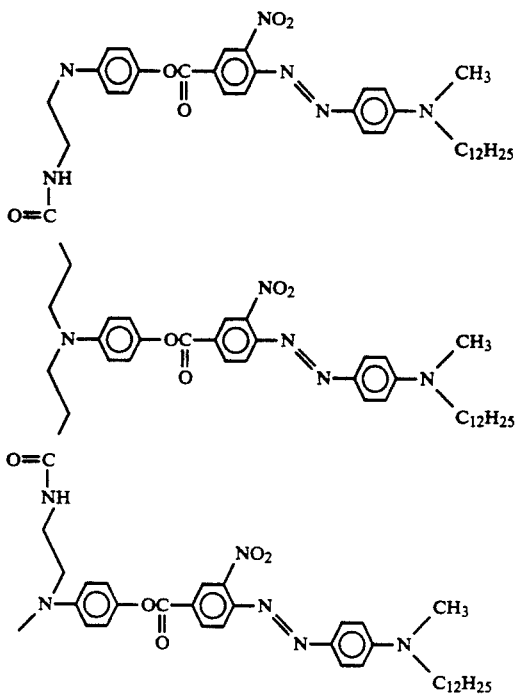

When the compounds are used for NLO applications it is possible to vary the refractive index by incorporating groups B, which have no NLO activity. Compounds having no NLO active groups B, may be used in combination with NLO active compounds.

Compound III below is an example of a compound containing at least one inactive group B. Suitable groups are alkyl phenyls and those used to produce liquid crystals such as biphenyl, phenyl benzoate, trans bicyclohexyl. These are attached to the polyamide backbone and hydrophobe via a linking group as described above. Where the compound contains NLO active chromophores or is intended for use in mixture to form a monolayer it is preferred that the length of the hydrophobic carbon chain is selected so that the average lengths of all groups B in the monolayer are approximately equal. The structure below is an example.

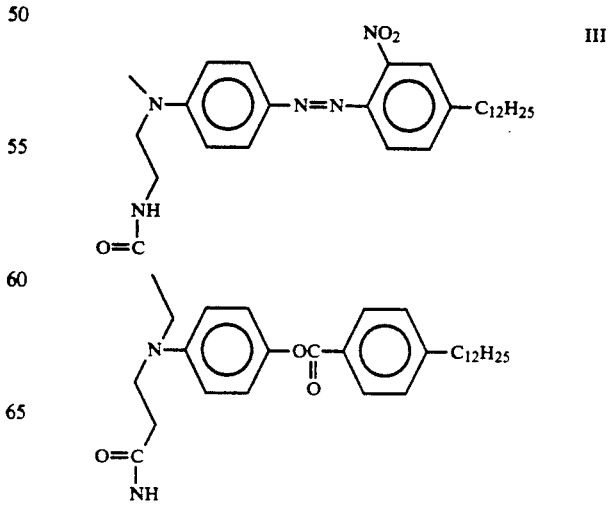

-continued

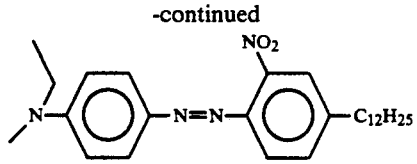

Moiety M may be included in the compounds of the invention using a diamine, diacid, diol or amino acid containing moiety M. This enables the production of compounds exemplified by IV in the form of random, alternating or block copolymers/oligomers. Moiety M may also be provided as a terminal group by the use of monofunctional compounds containing moiety M. These compounds enable films to be produced with at least two functions or properties. For example a film with both a large electro-optic coefficient due to the presence of NLO chromophores and that is photoconducting is obtained by introducing a molecular moiety that is able to photogenerate a charge such as a phthalocyanine. Suitable phthalocyanines include those described in European Patent Publications 262 761 and 155 780 and U.S. Pat. No. 4 606 895. Moieties that are able to transport and or trap charges may also be incorporated. This combination of functions provides a film that is photorefractive ie the refractive index of the film can be changed at wavelength x by illuminating the film at wavelength y. The structure shown below is an example.

required at intervals equal to one mono-molecular layer or vice versa.

The liquid commonly referred to as the sub-phase, is preferably an aqueous medium and the compressed mono-molecular layers are obtained by applying a compressing force to the composition deposited on the liquid surface, for example but not exclusively, using moveable dams in a Langmuir trough.

Suitable substrates include rigid and flexible substrates. The substrates may be transparent or reflective and may have additional layers or coatings to impart secondary or supportive properties such as conductivity and transparency as in the case of Indium/tin oxide coatings or may be an antireflection coating. Examples of suitable materials for rigid substrates include glass, quartz, semiconductor wafers of III/V materials or PMMA. Examples of flexible substrates include thin glass, polymer films such as PET or membrane materials such as sulphonated poly ethersulphone or ionomeric fluoropolymers. Additional layers may include reflective coatings such as aluminium or silver or may comprise coatings that contain zero or first order diffraction gratings.

The characteristics of the compounds as LB film forming materials can be characterised by techniques which are described by G L Gaines in "Insoluble Mono-layers at Liquid-Gas Interfaces", John Wiley and Sons, 1966 and by R A Hann, CH 2 "Molecular Structure and Properties" in "Langmuir-Blodgett Films", Edited G Roberts, Plenum, 1990.

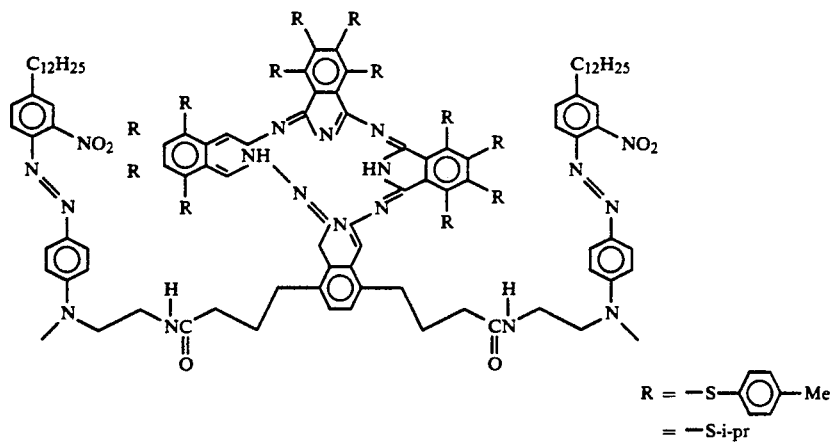

According to a further aspect there are provided monolayers containing varying concentrations of the compounds in the form of mixtures or copolymers providing periodic variations in properties.

According to a further aspect hybrid monolayers are provided containing more than one moiety each with more than one property.

According to a further aspect optical elements are provided in various forms capable of producing second order non-linear optical effects in a number of ways in various optical devices.

The method comprises passing a substrate into a liquid on the surface of which liquid is formed a compressed mono-molecular layer of the first composition and out of the liquid through the same or a second surface on which is compressed a mono-molecular layer of either the first composition or alternatively a second composition in the case where a non-centrosymmetric film is required or where compositional variation is The structure of the films can be characterised using techniques such as FTIR, and neutron scattering.

The excellent film forming and deposition characteristics of the compositions of the invention are believed to be due to a stable H-bonded structure formed at the amphiphilic interface. This H-bond interaction facilitates expulsion of water from the interface during multilayer film formation.

The properties of the films can be characterised as follows:

Characterisation Techniques—LB Films

Measurement of the nonlinear optical properties of LB film has been carried out using the technique of second harmonic generation, at a wavelength of either 1.06 $\mu$m or 1.91 $\mu$m. The technique is described, for example, by S Allen, "Materials for Nonlinear and Electro-optics", Inst. Pys. Conf. Ser. No. 133, (M H Lyons, ed.) IOP Publishing, 1989, pp163–174.

The refractive indices of LB films have been measured at a number of wavelengths using the method of Surface Plasmon Spectroscopy, as described by I Pockrand, J D. Swalen, J G Gordon and M R Philpott (Surface Science 74, 237-244, 1977).

Definitions—LB Films

The term "electro-optic coefficient" as employed herein refers to any component of the electro-optic tensor, $r_{ijk}$, as defined, for example in "Quantum Electronics" (2nd edition), by A Yariv (Wiley, N.Y. 1975), chapter 14.

Reduced tensor notation may be used, as described in "Physical Properties of Materials", by J F Nye (O.U.P. 1957), p. 247 (where the notation $z_{ijk}$ is used in place of the more usual $r_{ijk}$) to reduce the number of subscripts from three to two according to the convention:

$$r_{ijk} \rightarrow r_{mk}$$

with

| j,i | 1,1 | 2,2 | 3,3 | 2,3 | 1,3 | 1,2 |
|---|---|---|---|---|---|---|
| m | 1 | 2 | 3 | 4 | 5 | 6 |

The term "second harmonic coefficient" as employed herein refers to any component of the second-order nonlinear optical susceptibility $\chi^{(2)}(2\Omega; \Omega, \Omega)$, where $\Omega$ is the frequency of the fundamental optical wave. The term "d-coefficient" as used herein refers to any component of the related "d tensor", as defined, for example, in "Optical Waves in Crystals" by A Yariv and P Yeh (Wiley, N.Y., 1984), chapter 12. The second harmonic coefficient and d-coefficient are related by the expression $\chi^{(2)} = 2 \cdot d$ The term "active molecule" as employed herein refers to any molecule of the invention, or any other molecule, suitably functionalised for deposition in layers using the Langmuir Blodgett technique, and having a significant molecular nonlinearity $\beta$: preferably having $\beta$ greater than $10 \times 10^{-30}$ esu at the wavelength of interest.

The term "inactive molecule" as employed herein refers to any molecule, suitable for deposition in Langmuir Blodgett films, but not having a significant molecular nonlinearity $\beta$—i.e. having a value of $\beta$ less than $5 \times 10^{-30}$ esu at the wavelength of interest.

The term "molecular tilt angle" as employed herein refers to the average angle that the axis of the nonlinear optical component of an active molecule within an LB monolayer makes with the normal to the plane of the film.

Non-centrosymmetric films of the invention are suitable for use in optical switching devices (both electro-optic and all-optic), optical storage devices including memories, piezo and pyro-electric devices and synthetic biological membranes.

Films of the invention are suitable for use as optical elements in a range of optical devices. These devices, some of which are described below, are achievable due to the ability, using the molecules of the invention, to produce films of precise thickness, having predetermined values for the refractive index, electro-optic coefficient and other properties of interest. These properties can be specified on a monolayer scale throughout the thickness of the film, so that it is possible, for example, to build up a film with a specified refractive index profile across its thickness.

The refractive index, and electro-optic coefficient of a monolayer can be tailored to a specific requirement by one of a number of methods including:
a) Choice of one particular compound of the invention
b) Forming the monolayer from an intimate mixture of two or more of the compounds of the invention, producing a layer having refractive index and electro-optic coefficients intermediate between those of films of the constituent compounds.
c) Forming the monolayer from an intimate mixture of one or more of the compounds of the invention with other active or inactive compounds having substantially higher or lower refractive indices and/or electro-optic coefficients.

Since the thickness of an individual monolayer (typically about 3 nm) is much less than the wavelength of light, the refractive index of a multilayer film can be modified by varying the structure of the film on a monolayer scale. For example, if monolayers of two different materials, having different refractive indices, are deposited alternately then the resulting refractive index of the multilayer film produced will have a refractive index intermediate between the refractive indices of the two component monolayers.

In any given application it may be necessary to optimise one particular component of the electro-optic tensor of the deposited film. The relative magnitudes of different components of this tensor can be tailored to a specific requirement influencing the tilt angle of the component molecules of the film, using one of a number of methods including:
a) Choice of a particular compound of the invention. (Different compounds have, by virtue of their chemical structures, different tilt angles for their nonlinear-optical components with respect to the film normal.)
b) Formation of the monolayer from an intimate mixture of one or more of the compounds of the invention with other active or inactive compounds, such that the tilt angle of the molecule of the invention is modified by the addition of the other compounds.
c) Formation of the multilayer from monolayers of two or more different compositions deposited sequentially. The constituent monolayers will contain molecules having different molecular tilt angles, and thus have different relative magitudes for the electro-optic tensor coefficients. The coefficients for the multilayer film will be the average of the coefficient for the constituent monolayers.

An example of an application requiring control of the film properties as outlined above is the manufacture of optical filters having a narrow reflectivity band at a specified wavelength, in which this wavelength of maximum reflectivity can be tuned electro-optically.

Filters can be easily made from dielectric "stacks" (multilayers built up from films of alternating high and low refractive index). Fabrication is straightforward and narrow bandwidths can be achieved. However such filters are not tunable, and usually have large sidebands, which block out light at wavelengths other than the desired one. Better filters can be made by designing a required refractive index profiles through the thickness of the film. A Rugate filter consists in principle of a sinusoidal refractive index profile across the thickness of the film. In practice the sine-wave variation can be approximated by a number of step changes in refractive index. The performance of the filter is characterised by a number of properties as follows:

i) The optical density, or degree of rejection of the targeted wavelength. This should be as high as possible (100% rejection being the ultimate aim). The optical density is essentially determined by the number of periods within the film (i.e. its overall thickness).
ii) The bandWidth, or specificity. This is the narrowness of the rejection band, and is determined by the magnitude of the modulation ($n_p$) of the refractive index.
iii) Sideband rejection. It is not desirable to have sidebands, where light is rejected at wavelengths other than the targeted one. Sidebands are totally rejected if the refractive index profile is a pure sine wave, and so the number of steps within a single period determines the quality of sideband rejection.
iv) The operational wavelength (i.e. centre of the rejection band) is determined by the optical thickness ($\epsilon nl$) of period of the refractive index profile.

The use of Langmuir Blodgett films to build up Rugate filters of this type has the following advantages. Firstly the precise thickness control obtained by the LB deposition technique allows for accurate building up of the Rugate structures, and the ability to control the composition on a monolayer scale means that in principle a very good approximation to the desired sinusoidal refractive index profile could be achieved. Use of electro-optic materials within the layers can give the desired tunability. For example, mixtures of an electro-optic and an inactive material could be used. The ratio of active to inactive molecules in any layer would determine the refractive index and the electro-optic coefficient of that layer. Application of an electric field across the film would modify the refractive indices of the layers via the electro-optic effect. This would change the optical path length of the period, and hence the operational wavelength for the filter.

In order to achieve the required optical density for such a filter many LB monolayers will have to be deposited, to reach a total film thickness of at least several micrometers. For operation with light incidental normal to the plane of the film, and with the electric field applied between transparent electrodes deposited on either side of the film, the response will be optimised by maximising the electro-optic coefficient $r_{13}$, where the 1-axis lies within the plane of the film and the 3-axis along the normal to the plane of the film. This coefficient will be maximised by utilising monolayers in which the nonlinear optical component of the compound has a tilt angle of approximately 55 degrees with respect to the film normal.

A second example of an application requiring optimisation of refractive indices and electro-optic coefficients, as well as the precise thickness control offered by the Langmuir Blodgett deposition technique is the manufacture of a Fabry-Perot electro-optic modulator. The principle of such a device is described, for example, by C A Eldering, S T Kowel, M A Mortazavi and P F Brinkley (Applied Optics, vol. 29, no. 8, p1142, 1990). As in the example above, for operation with light incident normal to the plane of the film, the $r_{13}$ electro-optic coefficient should be optimised.

Thus first products of the invention comprise films "sandwiched between electrodes" for use as electroactive filters in telecommunication devices in which transmitted or reflected signals are controllable at high speeds.

Further applications of the molecules of the invention are based on their inclusion in "multifunctional" Langmuir Blodgett films, where the electro-optical and nonlinear optical properties of the molecules are combined with other properties, derived either from the molecules of the invention themselves, or from other molecules which may be mixed intimately with the molecules of the invention, within a single monolayer, or deposited as monolayers themselves sequentially with layers of the molecules of the invention.

An example of such a multifunctional film is a film having photorefractive properties. A thorough description of the photorefractive effect in inorganic crystals is given for example in "Electro-optic and Photorefractive Materials" (P Gunter, ed., Springer Verlag, New York, 1987). Such effects may be seen in organic films that have both photoconducting and electro-optical properties. Such films can be obtained using the Langmuir Blodgett technique to deposit molecules of the invention and other charge generating and charge transport molecules in a number of ways, including Deposition of monolayers containing an intimate mixture of the above molecules.

Sequential deposition of monolayers that individually comprise of a single one of the above molecules.

Deposition of a repeated monolayer sequence comprising for example of $p_1$ monolayers of the electro-optic molecule, followed by $p_2$ monolayers of the charge generating molecule followed by $p_3$ molecules of the charge transport molecule, where $p_1$, $p_2$ and $p_3$ are integers.

Thus the invention includes products comprising a hybrid multifunctional material with photoconducting and electro-optical properties that is photorefractive. Such products are suitable for use in optical filters whose transmissive or reflective properties at certain wavelengths can be controlled by addressing the filter with light at different wavelengths.

The invention is further described with reference to the following examples.

PREPARATION 1

4-Dodecyl-2-nitrobenzenediazonium chloride

4-Dodecyl-2-nitroaniline (61.20 g; 20 mol) was stirred with glacial acetic acid (200 ml) and propionic acid (200 ml) containing concentrated hydrochloric acid SG1.18 (100 ml) at 70° C. The amber solution was cooled to 0° C. and a solution of sodium nitrite (14.00 g; 0.203 mol) in water (100 ml) was added dropwise over 1 hour at 0° C. After stirring for 2 hours at 0° C. the excess nitrous acid was destroyed by the addition of 10% sulphamic acid to give an orange mixture.

PREPARATION 2

4-Dodecyl-2-nitro-4'-N,N,-bis-2-methoxycarbonylethyl aminoazobenzene

To a stirred solution of N,N-di-2-methoxycarbonylethylaniline (26.50 g ; 0.10 mol) in water (200 ml) containing concentrated hydrochloric acid (50 ml), 4-dodecyl-2-nitrobenzene diazonium mixture (0.10 mol) was added rapidly at <5° C. The red solution was neutralised by the addition of sodium acetate and stirred overniqht. The resulting mixture was filtered and washed with water (2,000 ml). The residue was dissolved in dichloromethane (400 ml) and washed with water (3×400 ml). The organic extracts were dried (Mg $SO_4$) and the solvent removed by evaporation under reduced pressure to give (crude product, 45.25 g;78%) a red oil/solid.

The crude product was purified by flash chromatography eluting with hexane, dichloromethane and chloroform to give an orange solid (34.76 g; 60%) m.p. 40°-42° C.

¹Hnmr (CDCl₃; 250 MHz; TMS) 0.70 t (3H), 1.18-1.72 (20H), 2.52-2.82 m (6H), 3.64-3.90 m (10H), 6.74 d (2H), 7.32-7.94 (5H).

ir (KBr disc) 2920, 1736, 1599, 1513, 1368, 1146, 831 cm⁻¹.

m/z 582 (m)+.

Analysis found C, 66.5; H,8.7; N,9.5.

$C_{32}H_{46}N_4O_6$ requires C, 65.96; H,7.96; N,9.6%.

PREPARATION 3

4'(N,N-bis-2-carboxyethtlamino)-4-dodecyl-2-nitroazobenzene

To a stirred mixture of the product of Preparation 2 (20.4 g; 0.035 mol) in 95% ethanol (100 ml), 10% (w/v) sodium hydroxide solution (50 ml) was added and heated to reflux. After 2 hours stirring at reflux the reaction mixture was poured into ice/water (200 g) with stirring diluting with more water to give 600 ml total volume and the pH adjusted to pH 1.0 by the addition of concentrated hydrochloric acid SG 1.18. The resulting mixture was filtered and washed with water (1,000 ml) then dried (60° C. vac oven) to give an orange-red solid (17.40 g;90%) m.p. 125°-128° C.

¹H nmr (DMSO⁻ᵈ⁶; 90 MHz; TMS) 0.95 t (3H) 1.03-1.70 m (20H) 2.35-2.82 m (6H), 3.46-3.92 mg (4H), 6.72 d (2 H), 7.40-7.84 m (5H).

ir (KBr disc) 2920, 1703, 1602, 1158, 820 cm⁻¹.

Analysis found C, 61.5; H, 7.8; N, 9.3.

$C_{30}H_{42}N_4O_6$ requires C, 64.96, H, 7.63; N, 10.10%.

EXAMPLE 1

7,13-Dioxo-2,18-bis-phenyl-10-[4-(4-dodecyl-2-nitrophenylazo) phenyl]-2,6,10,14,18-pentaazanonadecane To a stirred mixture of the product of Preparation 3 (5.55 g;0.010 mol) N-3-aminopropyl-N-methylaniline (3.28 g; 0.020 mol) and 1-hydroxybenzotriazole (2.70 g; 0.020 mol) in dry dichloromethane (100 ml) was added dicyclohexyl carbodimide (4.53 g; 0.022 mol) and 4-dimethylaminopyridine (DMAP) (0.01 g). After stirring overnight the mixture was filtered and the filtrate washed with water (2×200 ml).

The resulting organic extract was dried (MgSO₄) and the solvent removed by evaporation under reduced pressure to give an orange solid (crude product, 8.33 g; 98%).

The crude product was purifed by flash chromotography eluting with hexane, dichloromethane and finally chloroform increasing the polarity with methanol to give an orange solid (5.47 g; 65%) m.p. 104°-105° C.

¹Hnmr (CDCl₃; 90MH₂, TMS) 0.90 t (3H), 1.12-190 m (24H), 2.40 t (4H), 2.70 t (2H), 2.84 S (6H), 3.12-340 m (8H), 370 t (4H), 6.12 m (2H), 6.60-6.82 m (8H), 7.10-7.86 m (9H).

m/z (CI) 847 (M+H)+.

ir (KBr disc) 3312, 2923, 1639, 1601, 1149, 745 cm⁻¹.

Analysis C, 70.5; H,8.4; N, 12.8.

$C_{50}H_{70}N_8O_4$ requires C, 70.89; H,8.33; N,13.23%.

EXAMPLE 2

7,13-Dioxo-2,10,18-tris-[4-(4-dodecyl-2-nitrophenylazo) phenyl]-2,6,10,14,18-pentaazanonadecane To a stirred solution of the product of Example 1 (2.50 g; 2.95 mmol) in acetone (50 ml) and methanol (50 ml) containing hydrochloric acid SG 1.18 (5 ml), 4-dodecyl-2-nitrobenzenediazonium mixture (5.9 mmol) was added rapidly at <5° C. The mixture was neutralised by the addition of saturated sodium acetate solution and then stirred for 1 hour. The resulting mixture was filtered and washed with water (600 ml) and then dried (60° C. vac oven) to give (crude product, 4.12 g; 94%) an orange solid. The crude product was purified by flash chromatography, eluting with dichloromethane and chloroform and then recrystallised from a mixture of chloroform and hexane (1:1) to give after drying (60° C. vac oven) a red solid (0.1115 g) m.p. 132°-133° C.

¹Hnmr values (CDCl₃; 250 MHz; TMS) 0.90 t (9H), 1.10-1.80 m (64H), 2.48 t (4H), 2.70 t (6H), 2.96 s (6H), 3.23 q (4H), 3.34 t (4H), 3.71 t (4H), 625 m (2H), 6.59-6.77 m (6H), 7.35-7.80 m (15H).

ir (KBr disc) 3291, 2927, 1638, 1601, 1151, 817 cm⁻¹.

Analysis found C, 69.9; H, 8.7; N, 13.1.

$C_{86}H_{124}N_{14}O_8$ requires C, 69.69; H,8.43, N,13.23%.

PREPARATION 4

N-2-tert-butoxycarbonylaminopropyl-N-methylaniline

N-3-aminopropyl-N-methylaniline (8.20 g, 0.05 mmol) was dissolved in dichloromethane (100 ml) and the solution ᵥ cooled to 5°-10° C. Then a solution of di-tert-butyl ⎽ ⎽arbonate (10.90 g, 0.05 mmol) in dichloromethane (100 ml) was added dropwise with stirring. When the addition was finished, the solution was allowed to stir at room temperature for 20 hours. The reaction solution was washed with water (3×100 ml), dried (Na₂SO₄), and evaporated to dryness to give an oil (12.95 g, 98%). After a night in the fridge this oil became a low melting white-beige solid (m.p. 37°).

¹Hnmr (CDCl₃, 250 MHz, TMS) 1.46 (9H, s); 1.72 (2H,m); 2.91 (3H,s); 3.10 (4H,m); 4.70 (1H,m, NH); 6.50-7.42 (5H, m)

ir (nujol): 3349, 1683, 1601, 1460 cm⁻¹.

m/z (FAB): 265 (M+H)+.

PREPARATION 5

4-Dodecyl-4'-(N-2-tert-butoxycarbonylaminopropyl-N-methyl)-2-nitroazobenzene To a stirred solution of N-2-tert-butoxycarbonylaminopropyl-N-methylaniline (5.28 g; 0.020 mol) in methanol (200 ml), 4-dodecyl-2-nitrobenzenediazonium mixture (0.020 mol) was added rapidly at <5° C. The mixture was neutralised by the addition of sodium acetate and then stirred overnight. The resulting mixture was filtered, washed with water and then dried (air) to give an orange solid (crude product, 10.20 g, 88%).

The crude product was purified by flash chromatography eluting with hexane gradually increasing the polarity with dichloromethane to give an orange solid (5.14 g, 44%) m.p. 71°-72° C.

¹Hnmr (CDCl₃; 250 MHz;TMS) 0.97 t (3H), 1.26 s (9H), 1.40-1.92 m (22H), 2.70 t (2H), 3.02-3.24 m (5H), 3.47 t (2 H), 4.60 m (1H,D₂O exchangeable) 6.72 d (2H), 7.30-7.92 m (5H).

ir (KBr disc)

m/z 581 (m)+.

Analysis found C, 68.4; H, 9.2; N, 11.7.

$C_{33}H_{51}N_5O_4$ requires C, 68.13; H 8.84; N, 12.04%.

PREPARATION 6

4'-(N-3-aminopropyl-N-methylamino)-4-dodecyl-2-nitroazobenzene

To a stirred solution of 4'-(N-3-tert-butoxy carbonylaminopropyl)-4-dodecyl-2-nitroazobenzene (2.89 g; 4.97 mmol) in dichloromethane (100 ml), trifluoroacetic acid (6 ml) was added. After stirring overnight at room temperature 2N sodium hydroxide solution (100 ml) was added maintaining the temperature at <20° C. by the addition of ice when necessary. The organic phase was separated and washed with 2N sodium hydroxide solution (100 ml) and water (2×100 ml). The organic extracts were dried (MgSO$_4$) and the solvent removed by evaporation under reduced pressure to give an orange solid/liquid (crude product 1.93 g, 81%).

The crude product was purified by flash chromatography eluting with chloroform gradually increasing the polarity with methanol to give a red solid oil (1.00 g; 42%)

$^1$H nmr (CDCl$_3$; 90 MHZ; TMS) 0.90 t (3H) 1.12–1.96.

m (22H), 2.58–3.08 m(9H), 3.50 t (2H), 6.72 d (2H), 7.30–7.92 m (5H).

i.r. (KBr disc) 3366, 2932, 1602, 1518, 1383, 1147, 818 cm$^{-1}$.

m/z 481 (m)$^+$.

Analysis found C, 66.9; H, 9.0; N, 13.3.

C$_{28}$H$_{43}$N$_5$O$_2$ requires C,69.82; H, 9.00, N, 14.54%.

EXAMPLE 3

7,13-Dioxo-2,10,18-tris-[4-(4-dodecyl-2-nitrophenylazo)phenyl]-2,6,10,14,18-pentaazanonadecane (Alternative Preparation)

To a stirred mixture of 4'-(bis-N-2-carboxyethylamino)-4-dodecyl-2-nitroazobenzene (0.33 g; 0.60 mmol) 4'-(N-3-aminopropyl-N-methylamino)-4-dodecyl-2-nitroazobenzene (0.58 g; 1.20 mmol) and 1-hydroxybenzotriazole (0.16 g; 1.20 mmol) in dry dichloromethane (50 ml), dicyclohexylcarbodiimide (0.27 g; 1.30 mmol) and DMAP (0.01 g) were added. After stirring overnight at room temperature, the mixture was filtered and the filtrate washed with water (2×100 ml). The resultign organic extracts were dried (MgSO$_4$) and the solvent removed under reduced pressue to give (crude product, 0.34 g; 38%).

The crude product was purified by flash chromatography eluting with dichloromethane and then chloroform gradually increasing the polarity with methanol to give a dark red solid (0.10 g; 11%) m.p. 123°–126° C.).

PREPARATION 7

N-(2-Carboxyethyl)-N-methylaniline

Acrylic acid (36.03 g; 0.5 mol) was added to N-methylaniline (53.58 g; 0.5 mol) and an exothermic reaction took place after which reaction was virtually complete. The mixture was stood overnight at room temperature and then diluted with water and made alkaline by the addition of sodium carbonate. The mixture was washed with dichloromethane and then the aqueous layer was cautiously acidified to pH 4.5 by the addition of concentrated hydrochloric acid SG 1.18. The resulting mixture was extracted into dichloromethane and washed with water The organic extract was dried (MgSO$_4$) and the solvent removed by evaporation under reduced pressure to give a pale brown oil (57.32 g; 64%).

$^1$H nmr (CDCl$_3$; 250 MHz; TMS) 2.65 t (2H), 2.90 s (3H), 3.65 t (2H), 6.70–6.83 m (3H), 7.20–7.30 m (2H), 11.15 (6 s (1H, D$_2$O exchangeable)).

ir (thin film) 2915, 1714, 1601, 1501, 1193, 750, 693 cm$^{-1}$.

m/z 179 (m)$^+$.

PREPARATION 8

5-Oxo-2,10-diphenyl-2,6,10-triazaundecane

To a solution of N-2-carboxyethyl-N-methylaniline (10 g, 55.80 mmol), N-3-aminopropyl-N-methylaniline (916 g, 55.80 mmol), dicyclohexylcarbodiimide (11.52 g, 55.80 mmol) 1-hydroxybenzotriazole (7.53 g, 55.80 mmol) in dichloromethane (100 ml) was added DMAP (0.01 g). The reaction was exothermic and instantaneous. The reaction was allowed to stir at room temperature for 6 hours and then filtered. The filtrate was evaporated to dryness under reduced pressure and then the resulting residue was treated with acetone (2×30 ml), and the filtrates were combined. This resulting solution was evaporated to give a crude oil which was purified by flash chromatography, eluting with hexane, and then chloroform gradually increasing the polarity with methanol to give a yellowish oil (14.14 g, 78%).

$^1$H nmr (CDCl$_3$, 250 MHz. TMS) 1.70 (2H, m), 2.35 (2H, t), 2.85 (3H, s), 2.90 (3H, s), 3.25 (4H, m), 3.65 (2H, t), 5.95 (1H, m)m 6.60–6.80 (6H, m)m 7.10–7.30 (4H, m).

ir (KBr disc) 3295, 1640, 1600 cm$^{-1}$.

m/z (FAB): 326 (M+H)$^+$.

EXAMPLE 4

5-Oxo-2,10-di[4-(4-dodecyl-2-nitrophenylazo) phenyl]-2,6,10-triazaundecane

To a stirred solution of 5-oxo-2,10-diphenyl-2,6,10-triazoundecane (3.25 g; 0.01 mol) in acetone (200 ml), 4-dodecyl-2-nitrodiazonium mixture (0.02 mol) was added rapidly at <5° C. The resulting solution was neutralised by the addition of saturated sodium acetate solution. After stirring for 2½ hours the mixture was filtered and washed with water (1,000 ml) to give after drying (40° C. vac oven) an orange solid (crude 9.16 g; 95%).

The crude product could be purified by recrystallisation from chloroform; hexane (1:3) to give an orange solid (m.p. 95.5°–96.5° C.).

$^1$Hnmr (CDCl$_3$; 250 MHz; TMS) ).0.92 t (6H), 1.20–1.73 m (40H) 1.80 m (2H), 2.43 t (2H), 2.70 t (4H), 2.98 s (3H), 3.08 s (3H), 3.25 q (2H), 3.40 t (2H), 3.75 t (2H), 5.85 t (1H), 6.62–6.73 m (4H), 7.37–7.82 m (10H).

m/z (Fab) 960 (M+H ion cluster)$^+$.

Analysis found C,71.0; H,8.7; N,12.9.

C$_{56}$H$_{81}$N$_9$O$_5$ requires C,70.04; H,8.50, N, 13.13%.

PREPARATION 9

5,13-Dioxo-2,9,16-triphenyl-2.6,9,12,16-pentaazaheptadecane

To a stirred solution of N,N-bis-2-aminoethyl aniline (1.79 g; 0.01 mol), N-2-carboxyethyl-N-methylaniline (3.58 g; 0.02 mol) and 1-hydroxybenzotriazole (2.70 g; 0.02 mol) in dry dichloromethane (100 ml), dicyclohexycarbodiimide (4.53 g; 0.022 mol) and DMAP (0.01 g) were added. After stirring overnight the reaction mixture was filtered and the filtrate washed with water (2×200 ml). The organic extract was dried (MgSO$_4$)

and the solvent removed by evaporation under reduced pressure to give brown oil (crude product, 5.67 g >100%).

The crude product was purified by flash chromatography eluting with hexane and then chloroform gradually increasing the polarity with methanol to give an amber viscous oil (1.95 g; 39%).

¹Hnmr (CDCl₃; 250 MHz; TMS) 2.38 t (4H), 2.85 s (6H), 3.30–3.42 m (8H), 3.62 t (4H), 6.30–6.40 m (2H), 6.68–6.80 m (9H), 7.18–7.30 m (6H).

ir (thin film) 3295, 1642, 1599, 1503, 1365, 749 cm⁻¹.

m/z (Fab) 501 (M+H)⁺.

EXAMPLE 5

5,13-Dioxo-2,9,16-tris-[4-(4-dodecylphenyl)]-2,6,9,12,16-pentaazaheptadecane

To a stirred solution of 5,13-dioxo-2,9,16-triphenyl-2,6,9,12,16-pentaazaheptadecane (1.30 g; 2.59 mmol) in acetone (100 ml), 4-dodecyl-2-nitrobenzenediazonium mixture (7.78mmol) was added rapidly at <5° C. The mixture was then neutralised by the addition of sodium acetate. After stirring overnight the mixture was extracted into dichloromethane (2×100 ml) and washed with water (2×200 ml). The resulting organic extract was dried (MgSO₄) to give after solvent evaporation an orange oil (3.53 g; 94%).

The crude product could be purified by recrystallisation from chloroform:hexane (3:1) to give a red solid.

¹Hnmr (CDCl₃; 250 MHz; TMS) 0.89 t (9H), 1.20–1.83 m (60 H), 2.40 t (4H), 2.62–2.73 m (6H), 2.93 s (6H), 3.30–3.40 m (8H), 3.63–3.70 m (4H), 6.60–6.78 m (8H), 7.37–7.80 m (15H).

Analysis found C, 69.0; H, 84; N, 12.9.

$C_{84}H_{120}N_{14}O_8$ requires C, 69.39; H, 8.32; N, 13.49%.

PREPARATION 10

4-(N-2-aminoethyl-N-methyl)-2'-dodecyl-4'-nitroazobenzene

To a stirred solution of N-2-aminoethyl-N-methylaniline hydrochloride (3.78 g; 0.02 mol) in water (100 ml), 4-dodecyl-2-nitrobenzenediazonium mixture (0.02 mol) was added rapidly at <5° C. The mixture was neutralised by the addition of anhydrous sodium acetate. After stirring overnight the mixture was filtered, washed with water (500 ml) to give after drying (50° C. vac oven) a gummy solid (8.94 g; 96%).

¹H nmr (DMSO$^{d6}$; 90 MHz; TMS) 0.86 t (3H), 1.10–1.70 (20H)m, 2.60–3.00 m (4H), 3.08 s (3H), 3.63 t (2H), 6.80–7.00 m (2H), 7.55–7.80 m (5H).

ir (KBr disc) 3376, 2921, 1602, 1517, 1381, 1149, 821 cm⁻¹.

M/Z 467 (M)⁺.

EXAMPLE 6

6,12-Dioxo-2,9,16-tris-[4-(4-dodecyl-2-nitrophenyl azo)phenyl]-2,5,9,13,17-pentaazaheptadecane To a stirred mixture of 4-(N,N-bis-carboxy ethylamino)-4'-dodecyl-2'nitroazobenzene (1.17 g; 2.10 m mol), 4-(N-2-aminoethyl-N-methylamino)-4'-dodecyl-2'-nitroazobenzene (1.99 g; 4.20 mmol) and 1-hydroxybenzotriazole (0.57 g, 4.20 mmol) in dry dichloromethane (50 ml) dicyclohexylcarbodiimide (0.96 g; 4.66 m mol) and DMAP (0.01 g) were added. After stirring overnight the reaction was incomplete hence more dicyclohexylcarbodiimide (0.96 g, 4.66 m mol) and DMAP (0.01 g) was added and stirred for a further 24 h and then diluted with dichloromethane (100 ml), filtered. The resulting filtrates were washed with water (2×100 ml) and then dried (MgSO₄) and the solvent removed by evaporation under reduced pressure to give a brown orange solid (crude product 2.69 g; 88%).

The crude product was purified by flash chromatography, eluting with dichloromethane followed by recrystallisation from 95% ethanol to give after drying (40° C. vac oven) an orange solid, m.p. 127°–129° C.

¹Hnmr (CDCl₃; 250 MHz; TMS) 0.85 t (9H), 1.15–1.70 m (60H), 2.30 t (4H), 2.62–2.72 m (6H), 3.00 s (6H), 3.32–3.60 m (12H), 6.05–6.20 m (2H), 6.60–6.78 m (6H), 7.32–7.42 m (3H), 7.54–7.63 m (6H), 7.75 d (6H).

ir KBr disc) 3300, 2922, 1642, 1603, 1151, 823 cm⁻¹.

m/z (FAB) 1454 (m+H ion cluster)⁺.

EXAMPLE 7

7,13-Dioxo-2,10,18-tris-(10-cyano-3,8-dimethyl-10-dodecyloxycarbonyldecane-1,3,5,7,9-pentaenyl)-2,6,10,14,18-pentaazanonadecane This compound was made in four steps as detailed below.

Step 1

N,N-bis-2-carboxyethylaniline (3 g; 12.6 mmol), dicyclohexylcarbodiimide (5.22 g; 25.21 mmol), 1-hydroxybenzotriazole (3.41 g, 25.3 m mol), DMAp (0.01 g) and N-3 amino propyl-n-methylaniline (4.15 g; 25,20 mmol) were stirred with dichloromethane (80 ml). The reactor mixture was allowed to stir for 20 h at room temperature and then filtered. The solvent from the resulting filtrates was removed under reduced pressure. The resulting residue was treated with acetone (50 ml), filtered and the filtrate was evaporated under reduced pressure to give an oil crude product (6.33 g, 95%).

The crude product was purified by flash chromatography, eluting with hexane gradually increasing the polarity with chloroform and then chloroform gradually increasing the polarity with methanol to give a colourless oil (4,84 g, 72%).

¹Hnmr values; (CDCl₃; 250 MHz; TMS) 1.70 m (4H); 2.35 m (4H), 2.70 s (6H), 3.25 m (8H), 3.55 t (4H), 6.10 t (2H)m 6.55–6.85 m (10H)m 7.05–7.30 m (5H)

ir (thin film); 3399, 1639, 1599, 1500 cm⁻¹.

m/z 529.

Analysis found C, 71.40; H, 8.40; N, 13.00 .

$C_{32}H_{43}N_5O_2$ requires C, 72.55; H, 8.18; N, 13,29%.

Step 2

A solution of the compound prepared in Step 1 (7,13-Dioxo-2,10,18-triphenyl-2,6,10,14,18-pentaazanonadodecane) (4 g; 7.55 mmol), 40% aqueous formaldehyde (1.70 g; 22.65 mmol), triphenyl phosphine (5.94 g; 22.65 m mol), potassium iodide (3.76 g ; 22.65 mmol), acetic acid (4.49 g; 74.74 mmol), chloroform (100 ml) and water (5 ml) were stirred at room temperature for 10 days. Then 40% aqueous formaldehyde (1.70 g, 22.65 mmol) was added and the solution was allowed to stir at room temperature for a further four weeks. The resulting solution was diluted with water (100 ml) and extracted into chloroform (2×100 ml), washed with water (3×200 ml), dried (Na₂SO₄) and evaporated to dryness under reduced pressure. The resulting solid was washed with diethyl ether (5×100 ml) and filtered to give a solid (10.98 g; 84%) m.p. 133°–138° C.

¹Hnmr: (DMSO d⁶, 250 MHz, TMS) 1.50 m (4H), 2.25 m (4H), 2.80 s (6H), 3.00 m (8H), 3.25 m (4H), 5.00 d (6H), 6.35–8.05 m (59H).

ir (KBr disk): 3429, 1642, 1611, 1517, 1435, 1112 cm$^{-1}$.

m/z (FAB) 1608 corresponding to (M- I)+.

Analysis found C, 62.7; H, 5.5; N3.7; P,19.4; I,5.2.

$C_{89}H_{91}N_5O_2P_3I_3$ requires C, 61.56; H, 5.28; N,4.04, P,1.92; I,5.35%.

Step 3

Sodium methoxide (sodium 0.59 g; 25.91 mmol in 70 ml of dried ethanol) was added dropwise to a stirred solution of octa-2,4,6-triene-2,7-diol (2.02 g; 12.34 mmol) and the compound of step 2,7,13-dioxo-2,10,18-tris[4-(triphenyl-phosphoniomethyl) phenyl]-2,6,10,14,18-pentaazanonadecane triodide) (5 g; 2.87 mmol) in dimethyl formamide (1.80 ml) under nitrogen. The solution was allowed to stir at room temperature overnight, diluted with water (100 ml) and extracted with toluene (4×100 ml). The resulting tract was washed with water (2×100 ml), dried (MgSO$_4$) and evaporated under reduced pressure to give a dark red oil (crude product 6.25 g). The crude product was purified by flash chromatography, eluting with hexane, gradually increasing the polarity with ethyl acetate and finally ethylacetate gradually increasing the polarity with methanol to give a red solid (0.22 g, 8%) m.pt 116°-119° C.

$^1$Hnmr values : (CDCl$_3$, 250 MHz, TMS) 1.75 m (4H); 1.85 s (9H), 2.08 s (9H), 2.42 m (4H), 2.90 2 s (6H), 3.15-3.40 m (8H), 3.65 m (4H), 6.10 m (2H), 6.25-7.55 m (30H), 9.43 s (3H).

ir (KBr disc) ; 3401, 1657, 1611, 1561, 1180 cm$^{-1}$.

m/z (FAB) 1010 (ion cluster).

Analysis found C, 75.4; H, 8.1; N, 7.1.

$C_{65}H_{79}N_5O_5$ requires C, 77.26; H, 7.88; N, 6.93%.

Step 4

To a stirred red solution of the compound of Step 3 (7.13-dioxo-2,10,18-tris-[4-(3,8-dimethylocta-8-formyl-1,3,5,7-enyl) phenyl]-2,6,10,14,18-pentaazanonadecane) (0.17 g; 0.17 mmol) in toluene (25 ml) and chloroform (10 ml), piperidine (3 ml) and n-dodecylcyanoacetate (0.13 g; 0.51 mmol) were added. The solution was heated at reflux using a Dean and Stark for 3 h. The resulting violet solution was cooled and poured into water (50 ml) and extracted with chloroform (2×50 ml) and washed with water (3×50 ml). The organic extract was dried (Na$_2$SO$_4$) and the solvent removed by evaporation under reduced pressure to give a crude product (10.28 g, 95%).

The crude product was purified by flash chromatography eluting with hexane gradually increasing the polarity with chloroform and finally chloroform increasing the polarity with methanol to give a sticky violet solid.

$^1$Hnmr values; (CDCl$_3$; 250 MHz; TMS) 0.80 t (9H); 0.90-1.90 m (66H); 2.00 s (9H); 2.20 s (9H); 2.40 m (4H); 2.85 s (6H); 3.10-3.30 m(8H); 3.45-3.65 m (4H); 4.20 t (6H); 5.95-7.90 m (33H)

ir (KBr disc); 3389, 2216, 1712, 1643, 1603, 1515, 1177 cm$^{-1}$.

m/z (FAB) ion cluster at 1715 corresponding to (M+H)+.

COMPARATIVE EXAMPLE 1

4'-(N-2-acetylaminoethyl-N-ethylamino)-4-dodecyl-2-nitroazobenzene

To a stirred solution of N-2-acetylaminoethyl-N-ethylaniline (30.90 g; 0.15 mol) in acetone (300 ml), 4-dodecyl-2-nitrobenzenediazonium mixture (0.15 mol) was added rapidly at <5° C. The mixture was then neutralised by the addition of sodium acetate and stirred for 2 h and then filtered and washed with water. The resulting crude product was then purified by recrystallisation from 95% ethanol to give after drying (60° C. vac oven) an orange crystalline solid (56.70 g; 72%) mp 104°-105° C.

$^1$Hnmr values (CDCl$_3$; 90 MHz; TMS) 0.89 t (3H), 1.08-1.78 m (23H), 1.93 s (3H), 2.72 t (2H), 3.30-3.64 m (6H), 5.93 m (1H), 6.78 d (2H), 7.38-7.96 m (5H).

ir (KBr disc) 3265, 2919, 1642, 1600, 1510, 1144, 816 cm$^{-1}$.

Analysis found C, 69.3; H,9.2; N,12.8.

$C_{30}H_{45}N_5O_3$ requires C, 68.80; H,8.66; N, 13.37%.

EXAMPLE 8

The compound of Example 2 was evaluated to characterise the monolayer and to determine the efficiency of transfer using the LB technique. A small quantity of the material was accurately weighed out (+/−0.02 mgs) and made up to a 1.00 mg/ml solution in chloroform (ARISTAR from BDH). Using an 'Agla' all glass, micrometer syringe, a precisely measured quantity of this solution was applied to a clean water surface (Milli Q water of resistivity 10>ohms) in a glass Langmuir trough (Joyce-Loebl type IV). For the determination of surface pressure vs area ($\pi$-A) isotherms, the initial area allowed per molecule was 200Å$^2$. If the monolayer was to be used for dipping, 130Å$^2$ was allowed, since this makes a greater area of compressed monolayer available for transfer. In either case 5 mins were allowed for the chloroform to evaporate away before compression was started. When obtaining the $\pi$-A isotherm, the area was compressed to its minimum. The steepest region was extrapolated to give a value for the obtained are plotted in FIG. 1, giving an apm value of 103Å$^2$.

From the $\pi$-A isotherm a surface pressure of 30 mNm$^{-1}$ was chosen as a convenient dipping pressure. The monolayer was compressed to $\pi$=30 mNm$^{-1}$ and left for about 40 mins to ensure stability and to obtain a good baseline. The trough was provided with a "Control" function which uses a feedback loop to maintain $\pi$ constant by changing the area.

As a substrate for deposition, ordinary glass microscope slides were purchased unwashed from the manufacturer (Chance-Propper) and subjected to a rigorous cleaning procedure using ARISTAR solvents and Milli Q water, before being dried using oxygen free N$_2$ and stored for use.

For deposition, the slide was attached via a PTFE clamp to a micrometer which was motor driven, raising and lowering the slide (substrate) through the monolayer at a rate of 5 mmm/min.

On the first stroke, O↓, no material is transferred from the monolayer to the slide, since the slide is hydrophilic and passes through what is in effect a close packed monolayer of the hydrocarbon chains of the surface active molecule. On each subsequent stroke however, the slide and surface monolayer are of similar polarity and material is transferred. The area of the compressed monolayer on the surface must decrease to maintain a constant surface pressure during transfer. The change in position of the barriers can be followed on a plotter and converted to a change in area which is compared with the immersed area of the substrate. The deposition ratio is defined as:

| stroke | 0↓ | 1↑ | 2↓ | 3↑ | 4↓ | 5↑ | 6↓ | 7↑ | 8↓ | 9↑ |
|---|---|---|---|---|---|---|---|---|---|---|
| $d_x$, % | 0 | 106 | 38 | 97 | 76 | 110 | 81 | 97 | 81 | 97 |

$$\text{Deposition ratio } (d_x) = \frac{\text{Area of monolayer removed from from surface}}{\text{Area of substrate passed through the monolayer}}$$

For perfect transfer, the deposition ratio/substrate area should be 100±5%. The deposition ratios observed on the glass slides are given below.

| stroke | 0↓ | 1↑ | 2↓ | 3↑ | 4↓ | 5↑ | 6↓ | 7↑ | 8↓ |
|---|---|---|---|---|---|---|---|---|---|
| $d_x$, % | 0 | 100 | 83 | 100 | 91 | 100 | 91 | 100 | 95 |
| stroke | 9↑ | 10↓ | 11↑ | 12↓ | 13↑ | 14↓ | 15↑ | 16↓ | 17↑ |
| $d_x$, % | 95 | 91 | 99 | 95 | 95 | 91 | 99 | 91 | 104 |

SHG measurement, uv/vis absorption spectroscopy and FTIR on this material all indicated uniform thickness over the substrate and uniform increase in thickness with number of layers at least up to nine layers, i.e. the molecules within each layer appeared to be oriented with the chains perpendicular to the substrate, and each layer dipped Y-type.

Deposition of 17 layers was achieved. There was no reason to believe more layers cannot be deposited. The deposited material was yellow/orange and the colour sufficiently intense for one monolayer deposited on either side of a glass slide to be visible to the naked eye.

The refractive index, n, of multilayer films was measured using surface plasmon spectroscopy at three wavelengths. The wavelengths were 633, 820 and 1320 nm and the refractive indices were 1.680, 1.668 and 1.599 respectively. The electrooptic properties of a monolayer of the compound deposited on silver coated glass, were measured by surface plasmon resonance in the presence of a 3 kHz AC electric field of the order of $10^5$ V/m. The second order non linear optical susceptibility $\chi(2)=(240+90\,i)$ pm/V at 633 nm from which an r coefficient of 65 pm/V was obtained using the relationship $r = 2\,\chi\,(2)/n^4$.

EXAMPLE 9

The compound produced in Example 1 was evaluated by similar procedures to those used in Example 8.

Because of its shape and range, the $\pi$-A isotherm was obtained using three starting values of allowed area per molecule, namely 200, 100 and 120Å². The results are shown in FIG. 1. From the initial gradient, an average close packed apm of 102Å² was obtained (by extrapolating from this linear region back to the apm axis), which matches the value for Example 8. However, the isotherm then changed slope and extrapolating from this region gives a close packed apm of 78Å², suggesting that the ends of the backbone have "flipped up" off the water surface, thus reducing the area.

To dip this molecule, a surface pressure of 25 mNm$^{-1}$ was chosen as the highest stable pressure the monolayer could sustain. The deposition ratios for one glass substrate are given below.

COMPARATIVE EXAMPLE 2

The structurally related compound of Comparative Example 1 was investigated for monolayer formation and LB dipping properties.

Isotherms of this molecule were started at 70Å², and it has a close packed area per molecule of 47Å². The surface pressure rose to about 44 mNm$^{-1}$ before reaching a plateau, so a value of 30 mNm$^{-1}$ was chosen as a convenient dipping pressure. The deposition ratios obtained are shown below:

| stroke | 0↓ | 1↑ | 2↓ | 3↑ | 4↓ | 5↑ |
|---|---|---|---|---|---|---|
| $d_x$, % | 0 | 101 | −93 | 103 | −93 | 101 |

A negative value of $d_x$ means that the trough area had to increase to maintain the surface pressure constant, i.e. the film on the substrate peeled off and went back onto the water surface, showing that the molecule does not dip successfully at this chosen surface pressure.

EXAMPLE 10

The compound of Example 6 was examined to determine its monolayer and transfer properties. The backbone of this compound has two fewer methylene units than that of Example 2. The isotherm collapses at about the same surface pressure (as evaluated in Example 8). The area per molecule is very similar at 100Å² (cf 103Å² for Example 8). Seven layers were deposited by LB dipping with good transfer ratios.

| stroke | 0↓ | 1↑ | 2↓ | 3↑ | 4↓ | 5↑ | 6↓ | 7↑ |
|---|---|---|---|---|---|---|---|---|
| $d_x$, % | 0 | 102 | 88 | 109 | 88 | 107 | 90 | 100 |

EXAMPLE 11

The monolayer and transfer properties of the compound of Example 5 were examined.

The orientation of the amide groups in the backbone in this compound is reversed with respect to the compound of Example 6 and hence to that of Example 2. The number of methylenes in the backbone is the same as Example 6 and therefore two less than Example 2. This would not be expected to lead to a significant change in the close packed area per molecule compared to Example 2 and this was found to be the case, 103Å² for both molecules. In fact, the monolayer of the present polymer (Example 5) was somewhat more stable since it collapsed at a higher surface pressure (FIG. 1). Although the change in orientation of the amide groups might have altered the LB deposition this was very good.

| stroke | 0↓ | 1↑ | 2↓ | 3↑ | 4↓ | 5↑ | 6↓ | 7↑ | 8↓ | 9↑ |
|---|---|---|---|---|---|---|---|---|---|---|
| $d_x$, % | 0 | 104 | 95 | 100 | 95 | 109 | 95 | 100 | 104 | 109 |

EXAMPLE 12

The compound of Example 4 in which the backbone has been reduced to one amide link, but with two chromophoric groups attached was evaluated (FIG. 1). The surface pressure/area isotherm was still reasonable (FIG. 1), although as might be expected the area per molecule dropped to 77Å$^2$ Despite the major change in the backbone, the molecule still deposited effectively as an LB layer.

| stroke | 0↓ | 1↑ | 2↓ | 3↑ | 4↓ | 5↑ |
|---|---|---|---|---|---|---|
| $d_x$, % | 0 | 107 | 87 | 107 | 99 | 99 |

EXAMPLE 13

The compound of Example 7 was evaluated for its monolayer and transfer properties.

The polyene chains, ester-linked to the $C_{12}H_{25}$ hydrocarbon tail, resulted in a more fluid monolayer with a much larger area per molecule (about 156Å$^2$) than seen in Example 8, see FIG. 2. Nevertheless, the molecule was sufficiently stable at 30 mN$^{-2}$ to be deposited as an LB film. Nine layers were deposited, although the transfer ratio for the ninth layer could not be calculated.

| stroke | 0↓ | 1↑ | 2↓ | 3↑ | 4↓ | 5↑ | 6↓ | 7↑ | 8↓ | 9↑ |
|---|---|---|---|---|---|---|---|---|---|---|
| $d_x$, % | 0 | 83 | 97 | 92 | 90 | 92 | 88 | 92 | 74 | — |

PREPARATION 11

N,N-(2-biscarboxyethyl)-4-dodecylaniline

A mixture of 4-dodecylaniline (130.5 g, 0.50 mol) and acrylic acid (80 ml, 1.168 mol) containing water (10 ml) was stirred at 75° C. for 5 hours. After cooling, the mixture was diluted with water (200 ml) and then extracted into dichloromethane (2×200 ml). The resulting organic extract was washed with water (2×400 ml) and then dried (MgSO$_4$) and the solvent removed by evaporation under reduced pressure to give a brown oil (crude product, 150.0 g; 74%).

The crude product could be purified by stirring with dichloromethane and the resulting mixture filtered to give after drying a white solid mp 110°-113° C.

$^1$H nmr (CDCl$_3$; 250 MHz; TMS) 0.87 t (3H), 1.15-1.65 m (20H), 2.48-2.65 m (6H), 3.56 t (4H), 6.90 d (2H), 7.13 d (2H), 9.85 6 s (2H; D$_2$O exchangeable).
ir (KBr disc) 2920, 1702, 1518, 1177, 828 cm$^{-1}$.
m/z 405 (m)+.
Analysis found C, 70.6; H, 9.4; N, 2.9.
C$_{24}$H$_{39}$NO$_4$ requires C, 71.07; H, 9.69; N, 3.45%.

PREPARATION 12

N-(3-Cyanoethyl)-N-methyl-4-dodecylaniline

To a stirred mixture of N-(2-cyanoethyl)-4-dodecylaniline (1.56 g; 5.0 mmol) and triethylamine (0.70 ml; 5.0 mmol), methyl iodide (0.30 ml, 5 mmol) was added and heated at reflux. After 1½ hours the reaction was incomplete hence more methyl iodide (0.60 ml); 10 mmol) was added. After refluxing overnight the reaction was still incomplete thus more methyl iodide (0.90 ml; 14 mmol) was added. After a further 5 hours at reflux the reaction solution was cooled and diluted with water (100 ml) and extracted into dichloromethane (2×50 ml). The organic extract was washed with water (2×100 ml) and then dried (MgSO$_4$) and the solvent removed under reduced pressure to give a brown oil (1.00 g; 62%).

$^1$Hnmr (CDCl$_3$; 250 mHz; TMS) 0.90 t (3H), 1.20-1.68 m (20H), 2.43-2.60 m (4H) 3.00 s (3H), 3.70 t (2H), 6.65 d (2H), 7.10 d (2H).
ir (thin film) 2923, 2248, 1614, 1517, 807 cm$^{-1}$.
m/z 328 (m)+.

PREPARATION 13

N-(3-aminopropyl)-N-methyl-4-dodecylaniline

A mixture of N-(3-cyanoethyl)-N-methyl-4-dodecylaniline (3.00 g; 9.13 mmol), liquid ammonia (5 g) and methanol (50 ml) and raney nickel (0.5 g) was heated at 130°-140° C. for 48 hours in an autoclave under 100 atms of hydrogen. The resulting mixture was filtered through clarcel flo and the filtrates diluted with water (100 ml) and extracted into CH$_2$Cl$_2$ (2×125 ml) and washed with water (2×250 ml). The organic extract dried (MgSO$_4$) and the solvent removed by evaporation under reduced pressure to give an amber liquid (crude product, 1.70 g, 56%)

The crude product was then purified by flash chromatography eluting with hexane then dichloromethane gradually increasing the polarity with methanol to give after drying a white solid (0.58 g; 19%) mp 74°-76° C.

$^1$Hnmr (CDCl$_3$; 250 MHz, TMS) 0.90 t (3H), 1.20-160M (20H, 1.78 m (2H), 2.40-2.58m (4H), 2.80 t (2H), 2.90 s (3H), 3.38 t (2H), 6.65 d (2H), 7.04 d (2H)
ir (KBr disc) 3274, 2921, 1615, 1467, 805 cm$^{-1}$.
m/z 332 (M)+.

EXAMPLE 14

7,13-Dioxo-2,10,18-tris-(4-dodecylohenyl)-2,6,10,14,18-pentaazanonadecane

To a stirred mixture of N,N-(bis-2-carboxyethyl)-4-dodecylaniline (0.33 g; 0.81 mmol) and N-(3-aminopropyl)-N-methyl-4-dodecylaniline (0.55 g; 1.66 mmol) and 1-hydroxybenzotriazole (0.11 g; 0.81 mmol) in dry dichloromethane (50 ml), dicyclohexycarbodiimide (0.18 g; 0.87 m mol) and DMAp (0.01 g) were added. After stirring overnight at room temperature, the mixture was filtered and the filtrates washed with water (2×100 ml). The resulting organic extracts were dried (MgSO$_4$) and the solvent removed under reduced pressure to give (crude product, 0.94 g 100%).

The crude product was purified by flash chromatography eluting with hexane and then dichloromethane gradually increasing the polarity with methanol followed by recrystallisation from 95% ethanol to give after drying (35° C. drying pistol under reduced pressure) a fawn solid (0.19 g; 23%) m.p. 63.5°-64.5° C.

$^1$H nmr (CDCl$_3$; 250 MHz; TMS) 0.90 t (9H), 1.20-1.63 m (60H), 1.72 m (4H), 2.35-2.58 m (10H), 2.80 s (6H), 3.25 m (8H), 3.55 t (4H), 6.05 m (2H), 6.58-710 m (12H).
ir (K Br disc) 3292, 1642, 1617, 802 cm$^{-1}$.
m/z (FAB) 1034 (M+H ion cluster)+.
Analysis found C,78.4; H,11.3 N,6.3.
C$_{68}$H$_{115}$N$_5$O$_2$ requires C,78.95; H,11.20; N,6.77%.

PREPARATION 14

N-(3-Cyanopropyl)-N-methyl-4-ethoxyaniline

To a stirred solution of 4-ethoxy-N-methylaniline (22.65 g;0.15 mol) in absolute ethanol (100 ml) 3-bromopropionitrile (16.6 ml, 0.20 mol) and triethylamine (21;0.15 mol) were added. After stirring at reflux for 18 hr the reaction solution was cooled, diluted with water (200 ml) and extracted into dichloromethane (2×200 ml) and washed with water (2×400 ml). The resulting organic extract was dried (Mg SO$_4$), the solvent was then removed under reduced pressure to give a brown oil (crude product 19.10 g;62%).

The crude product was purified by recrystallisation from 95% ethanol to give after drying (50° C. vac oven) a fawn crystalline solid m.p. 59–60% (12.74 g;42%).

$^1$Hnmr (CDCl$_3$;250 mHz;TMS) 1.38 t(3H), 2.53 t (2H), 2.95 s (3H), 3.65 t (2H), 3.98 q (2H), 6.70–6.78 m (2H), 6.83–6.90 t (2H).

m/z 204 (m)+.

Analysis C, 71.4; H 8.5 ; N, 13.5.

C$_{12}$H$_{15}$N$_2$O requires C, 70.56; H 7.90 ; N, 13.71%.

PREPARATION 15

N-3-Aminopropyl-N-methyl-4-ethoxyaniline

A mixture of N-3-cyanoethyl-N-methyl-4-ethoxyaniline (10.20 g;0.05 mol), liquid ammonia (10 g), methanol (100 ml) and raney nickel (2.0 g) was heated at 130° C. for 24 hr in an autoclave under 100 atms of hydrogen. The resulting mixture was filtered through clarcel flo and the solvent removed from the filtrates to give a brown oil (9.56 g; 91%) which solidified on standing m.p. 97°–98° C.

$^1$Hnmr (CDCl$_3$; 250 MHz; TMS) 1.40 t (3H), 1.80–2.00 m (4H), 2.85 s (3H), 3.32 m (2H), 4.00 q (2H), 6.65–6.90 m (4H).

m/z (CI) 209 (m+H+).

PREPARATION 16

7,13-Dioxo-2,18-bis-(4-ethoxyphenyl)-10-(4-hydroxyphenyl) -2,6,10,14,18-pentaazanonadecane To a stirred mixture of N,N-(bis-2-carboxyethyl)-4-hydroxyaniline (2.53 g; 0.01 mol), N-(3-aminopropyl-N-methyl-4-hydroxyaniline (4.16 g; 0.02 mol) and 1-hydroxybenzotriazole (2.70 g; 0.02 mol) in dry dichloromethane (50 ml), dicyclohexylcarbodiimide (4.55 g; 0.022 mol) and 4-dimethylaminopyridine (0.01 g) were added. After stirring over the weekend at room temperature, the mixture was filtered and the filtrates washed with water (3×100 ml). The resulting organic extracts were dried (MgSO$_4$) and the solvent removed under reduced pressure to give an oil (crude product 6.59 g; 100%).

The crude product was purified by flash chromatography eluting with dichloromethane gradually increasing the polarity with methanol to give a brown oil (2.22 g; 35%).

$^1$Hnmr (CDCl$_3$; 250 MHz; TMS) 1.38 t (6H), 1.73 m (4H), 2.30 t (4H), 2.78 s (6H), 3.10–3.35 m (12H), 3.97 q (4H), 6.62–6.8 m (14H).

ir (thin film) 3290, 2932, 1642, 1511, 1242, 815 cm$^{-1}$.

m/z (FAB) 634 (M +H ion cluster)+.

PREPARATION 17

7,13-Dioxo-2,10,18-tris-(4-hydroxyohenyl)-2,6,10,14,18-pentaazanonadecane

To a stirred solution of 7,13-dioxo-2,18-bis-(4-ethoxyphenyl)-10-(4-hydroxyphenyl) 2,6,10,14,18-pentaazanonadecane (1.10 g; 1.74 mmol) in dry dichloromethane (15 ml), 1.0 m boron tribromide in dichloromethane (35 ml; 35 mmol) was added dropwise at <5° C. over 5 min. The mixture was stirred at <5° C. for ¼ hr and then allowed to stir for a further 2 hr whilst warming to room temperature. The resulting mixture was cooled to 5° C. and the pH adjusted to pH11 by the addition of 14% (v/v) ammonia solution, then diluted with a further 50 ml dichloromethane. The mixture was allowed to stir for a further 1 hr then the liquors were decanted off leaving a residual oil which was dissolved in methanol, the solvent was then removed under reduced pressure to give a brown solid (1.00 g; 100%) m.p. 53°–55° C.

$^1$Hnmr (DMSO$^{d6}$; 250 MHz; TMS) 1.63 q (4H), 2.30 t (4H), 2.80 s (6H), 3.04 q (4H), 3.15–3.48 m (8H), 6.52–7.40 m (12H), 8.00 t (2H), 8.80 6 s (3H).

ir (kBr disc) 3159, 1642, 1513, 1237, 820 cm$^{31\ 1}$.

m/z (FAB) 578 (m+H ion cluster)+.

PREPARATION 18

4-Carboxy-4'-(N-dodecyl-N-methylamino)-2-nitroazobenzene

To a stirred mixture of 4-amino-3-nitrobenzoic acid (18.20 g; 0.10 mol) in water (500 ml) containing 47% sodium hydroxide solution (10 ml), concentrated hydrochloric acid (50 ml) was added. The resulting mixture was stirred at 0° C. and 2N sodium nitrite solution (60 ml; 0.12 mol) added. After stirring for 1 hr the excess nitrous acid was destroyed by the addition of 10% sulphamic acid solution. The resulting diazonium mixture was added rapidly to a stirred solution of N-dodecyl-N-methylaniline (27.50 g; 0.10 mol) in acetone (200 ml) at <5° C. The mixture was then neutralised by the addition of anhydrous acetate. After stirring overnight the mixture was filtered and washed with water to give after drying (40° C. vac oven) a red solid (crude product, 43.75 g ; 93%). The crude product was purified by recrystallisation from 95% ethanol to give after drying a purple/red crystalline solid 24.63 g; 53%) m.p. 157°–159° C.

$^1$Hnmr (CDCl$_3$; 250 MHz; TMS) 0.87 t (3H), 1.22–1.75 m (20H) 3.10 s (3H), 3.45 t (2H), 6.75 d (2H), 7.80–7.95 m (3H), 8.30dd (1H), 8.58 d (1H).

ir (KBr disc) 2923, 1685, 1377, 1247, 1145, 822 cm$^{-1}$.

m/z 468 (m)+.

Analysis Cm 67, ; H8.0; N,11.6.

C$_{26}$H$_{36}$N$_4$O$_4$ requires C, 66.64; H 7.74; N, 11.96%.

EXAMPLE 15

7,13-Dioxo-2,10,18-tris-{4-[4-(N-dodecyl-N-methylaminoohenylazo)-3-nitrobenzoyloxy]phenyl} pentaazanonadecane To a stirred mixture of 7,13-dioxo-2,10,18-tris-(4-hydroxyphenyl)-2,6,10,14,18-pentaazanonadecane (0.50 g; 0.87 mmol) and 4-carboxy-4'-(N-dodecyl-N-methylamino)-2-nitroazobenzene (1.20 g; 2.56 mmol) in dry dichloromethane (150 ml), dicyclohexylcarbodiimide (0.60 g; 2.91 mmol) and 4-dimethylaminopyridine (0.01 g) were added. After 68 hr the reaction had not gone to completion, thus more 4-carboxy-4'-(N-dodecyl-N-methylamino)-2-nitroazobenzene (0.60 g; 1.28 mmol), dicyclohexylcarbodiimide (0.30 g; 1.45 mmol) and anhydrous dimethyl formamide (20 ml) was added. After stirring for a further 20hr the mixture was filtered and the filtrates washed with water (3×200 ml), dried (MgSO$_4$) and the solvent removed under reduced pressure to give a red oil (crude product, 2.4 g; >100%).

The crude product could be purified by flash chromatography, eluting with dichloromethane, gradually increasing the polarity with methanol and then recrystallised from a mixture of hexane and dichloromethane (7:2) to give after drying (40° C. vac oven) a red solid m p. 99°-101° C.

$^1$Hnmr (CDCl$_3$; 250 MHz; TMS) 0.92 t (9H), 1.20–1.70 m (64H), 2.50 t (4H), 2.90 s (6H), 3.12 s (6H), 3.14 s (3H), 3.20–3.70 m (18H), 6.60–7.10 m (20H), 7.78–7.91 m (9H), 8.32 dd (3H), 8.60 d (3H).

ir KBr disc) 3294, 2923, 1730, 1638, 1600, 1238, 1147, 820 cm$^{-1}$.

m/z (FAB) 1930 (M +H$^+$ion cluster).

Analysis found C,68.3, H,7.7; N,11.8.

C$_{110}$H$_{143}$N$_{17}$O$_{14}$ requires C, 68.48; H,7.58; N,12.34%

EXAMPLE 16

Preparation of the condensation product of N,N-bis (2-aminoethyl)aniline and N,N-bis(2-methoxycarbonylethyl) aniline coupled with 4-dodecyl-2-nitrobenzenediazonium chloride A mixture of N,N-bis(2-aminoethyl)aniline 1.320 g;0.005 mol) and N,N-bis(2-methoxycarbonylethyl) aniline (1.32 g; 0.0051 mol) was heated to 165° C. for 30 minutes during which time the temperature dropped to 145° C. Bench vacuum was applied and the mixture was heated at 180°–190° C. for a further 2 hours. The mixture was cooled to room temperature and the glassy solid was dissolved in chloroform (20 ml). The chloroform solution was drowned into toluene (150 ml) and the liquor was decanted from the tarry, semi-solid residue. The residue was dissolved in a mixture of acetone and dimethyl sulphoxide (100/200 ml) and cooled below 5° C. A mixture of the 4-dodecyl-2-nitrobenzenediazonium chloride (0.057 mol) was added dropwise to the solution causing an immediate precipitation of tarry material. Sodium acetate was added to neutralise acidity and acetone/dimethyl sulphoxide (100/200 ml) was added and the mixture was stirred below 10° C. for 1 hour, then stood overnight.

The mixture was extracted with dichloromethane (300 ml) and the organic extract was washed with water (100 ml), saturated sodium bicarbonate solution (100 ml), and water (3×100 ml). After drying and filtration the organic solution was evaporated to give a tarry residue which was chromatographed (silica/dichloromethane/methanol) to give a solid. This material was dissolved in chloroform (20 ml) and added dropwise to hexane (600 ml). The resulting solid was filtered, washed with hexane and dried at 80° C. to give the title compound. (0.85 g) m.p. 154°–160° C.

ir (KBr 3296; 3073; 1731; 1648; 1599; 1358; 1150; 827 cm$^{-1}$

C$_3$H$_{33}$N$_4$O$_5$(C$_{58}$H$_{82}$N$_{10}$O$_6$)$_n$C$_{28}$H$_{32}$N$_6$O$_2$ requires C 68.7; H 7.5; N 13.7. Found C 67.8; H 8.6; N 13.0.

$^1$Hnmr (CDCl$_3$) broad resonances at 0.9, 1.3, 1.62, 2.4, 2.7, 3.2–3.8, 4.38 and 6.4–7.8.

The product was analysed using NAMAS accredited GPC chromatography. A sample was dissolved in THF (3 mg/ml) and passed through Polymer Laboratories PLGEL columns, calibrated using Polystyrene standards, at 0.5 ml/min at 24° C. The molecular weight distribution was obtained using a refractometer detection system. The number and weight average molecular weights were measured to be 3420 and 4540 respectively.

EXAMPLE 17

The compound of Example 14 in which the backbone is the same as in the compound of Example 2, but in which three hydrophobic chains are attached which contain (non-NLO active) chromophoric units was evaluated (FIG. 2). The surface pressure/area isotherm was very similar to that of Example 2 and the close packed area per molecule was identical at 103 Å$^2$. LB deposition was achieved from a monolayer held at 35 mNm$^{-1}$.

| Stroke | 0↓ | 1↑ | 2↓ | 3↑ | 4↓ | 5↑ |
|---|---|---|---|---|---|---|
| d$_x$, % | 1 | 100 | 92 | 96 | 87 | 92 |

A refractive index of 1.513 was obtained at 633 nm from a multilayer (25) film of the compound, using surface plasmon spectroscopy.

EXAMPLE 18

The compound of Example 15 was evaluated for its monolayer and transfer properties. The backbone of this molecule is the same as that found in Example 2. The acceptor and donor moieties of the chromophore are reversed with respect to Example 2 and are linked to the backbone via an ester. The surface pressure/area per molecule isotherm (FIG. 2) has a similar shape to that of Example 2, but a larger close packed area per molecule of 120Å$^2$ was observed. The monolayer was compressed to a surface pressure of 35 mNm$^{-1}$ for LB deposition at 19° C.

| Stroke | 0↓ | 1↑ | 2↓ | 3↑ | 4↓ | 5↑ |
|---|---|---|---|---|---|---|
| d$_x$, % | 0 | 107 | 99 | 103 | 99 | 99 |

EXAMPLE 19

The deposition of alternating layers of the molecules of Examples 2 and 14 was achieved by using a surface pressure for the compressed monolayers of 35 mNm$^{-1}$.

| Stroke | 0↓ | 1↑ | 2↓ | 3↑ | 4↓ | 5↑ | 6↓ | 7↑ |
|---|---|---|---|---|---|---|---|---|
| d$_x$, % | 0 | 98 | 90 | 97 | 88 | 95 | 91 | 95 |
| Stroke | 8↓ | 9↑ | 10↓ | 11↑ | 12↓ | 13↑ | 14↓ | 15↑ |
| d$_x$, % | 0 | 102 | 88 | 109 | 88 | 107 | 90 | 100 |

Ignoring the first down stroke (0↓), a monolayer of Example 2 was deposited on all upstrokes and a monolayer of Example 14 was deposited on all down strokes. In this way a non-centrosymmetric structure could be built up.

EXAMPLE 20

The compound of Example 16 was evaluated for its monolayer and transfer properties. The molecule contains approximately six chromophoric units. Its surface pressure/area per molecule isotherm has a similar shape to that of Example 2, but has a larger close packed area per molecule of 216Å$^2$. Monomolecular layers of this material could be deposited from a monolayer compressed to 30 mNm$^{-1}$.

| Stroke | 0↓ | 1↑ | 2↓ | 3↑ | 4↓ | 5↑ | 6↓ | 7↑ |
|---|---|---|---|---|---|---|---|---|
| d$_x$, % | 0 | 101 | 88 | 101 | 84 | 101 | 80 | 101 | or to 35 mNm$^{-1}$

| Stroke | 0↓ | 1↑ | 2↓ | 3↑ | 4↓ | 5↑ |
|---|---|---|---|---|---|---|
| d$_x$, % | 1 | 101 | 93 | 101 | 84 | 105 |

We claim:

1. A non-centrosymmetric bilayer comprising an amphiphilic material having the general formula

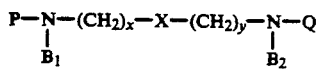

where X is selected from

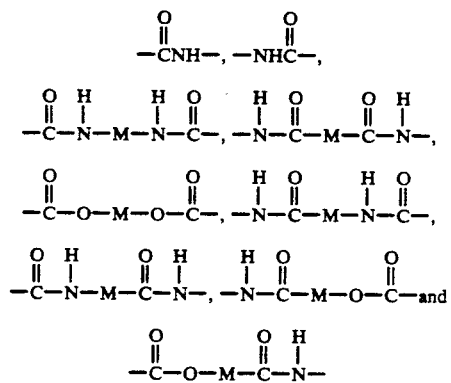

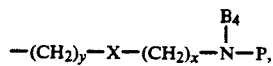

where M is a molecular moiety, x and y may be the same or different and are between 1 and 6, B$_1$ and B$_2$ may be the same or different and are chosen from phenyl, alkylphenyl or any molecular moiety made hydrophobic by attachment of a group containing from 8 to 40 carbon atoms, P is selected from a C$_1$ to C$_6$ alkyl group, —(CH$_2$)$_y$—X—(CH$_2$)$_x$—N—P,
  |
  B$_4$ Q is selected from a C$_1$ to C$_6$ alkyl group,

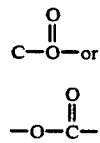

(CH$_2$)$_y$—X—M and —(CH$_2$)$_y$—Z—M where Z is either where B$_3$ and B$_4$ may be the same or different from B$_1$ and B$_2$ and are chosen from the same list of substituent groups with the proviso that when the compound contains only 2 nitrogen atoms in the chain both B$_1$ and B$_2$ must be molecular moieties made hydrophobic by attachment of a group containing 8 to 40 carbon atoms and when the compound contains only 3 nitrogen atoms at least one of B$_1$, B$_2$, B$_3$ or B$_4$ must be a molecular moiety made hydrophobic by attachment of a group containing 8 to 40 carbon atoms in which the amide groups of a first layer are adjacent to the amide groups of a second layer and in which the donor groups of an ordered arrangement of chromophores adjacent to an amide group in the first layer is aligned with a second layer in which the acceptor groups of an ordered arrangement of chromophores are adjacent to the amide groups, the chromophores in a given layer being the same or different and the layers optionally containing some non chromophore groups linked to the amide groups.

2. A bilayer according to claim 1 in which at least some of the pendant groups B$_1$, B$_2$, B$_3$ and B$_4$ include a chromophore group.

3. A bilayer according to claim 2 in which the chromophore group comprises a conjugated system (C) of $\pi$-bonds, substituted at or near one end by one or more $\pi$-electron acceptor groups (A) and at or near the other by a $\pi$-electron donor group (D), wherein the conjugated system (C) comprises aromatic ring systems, condensed aromatic ring systems, (poly)ene systems (one or more conjugated $\pi$-bonds), (poly)ene systems (one or more conjugated acetylene bonds), quinomethide systems, any of the above substituted by one or more heteroatom replacement(s) of a carbon atom(s), and/or by one or more heteroatom replacement(s) of a C=C double bond(s) and combinations of the above with or without heteroatom replacement(s).

4. A bilayer according to either of claim 2 or claim 3 wherein the $\pi$-electron donor substituent(s), (D), are selected from amino, NR$^1$R$^2$; thio, SR$^1$; oxy, OR$^1$; phosphino, PR$^1$R$^2$, where R$^1$ and R$^2$ are organic substituents selected from: alkyl, cycloalkyl, aryl, heteroaryl, alkenyl, cycloalkenyl, alkynyl, any of which may be optionally substituted and contain heteroatom replacements.

5. A bilayer according to either of claim 2 or claim 3 wherein the $\pi$-electron acceptor substituent(s), A, are selected from nitro, NO$_2$; cyano, CN; nitroso, NO; ester, CO$_2$R; amide, CONR$^1$R$^2$; ketone, COR$^1$; formyl, COH; sulphone, SO$_2$R$^1$; sulphoxide, SOR$^1$; sulphonate ester, SO$_3$R$^1$; sulphonamide, SO$_2$NR$^1$R$^2$; phosphonate, P(=O)OR$^1$OR$^2$; phosphine oxide, P(=O)R$^1$R$^2$: boronate ester, B(OR$^1$)OR$^2$; N-pyridinium and substituted variants, and other positively charged quaternary salts, heteroatoms especially N, when replacing carbon in an aromatic ring of the conjugated system, and quaternised versions of the same wherein R$^1$ and R$^2$ are organic moieties as previously defined.

6. A non-centrosymmetric bilayer comprising an amphiphilic material having the general formula

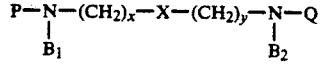

where X is selected from

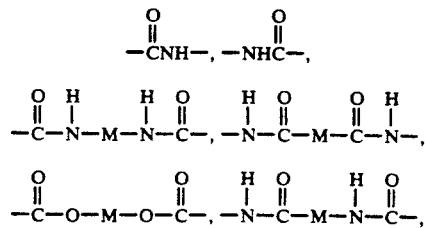

-continued

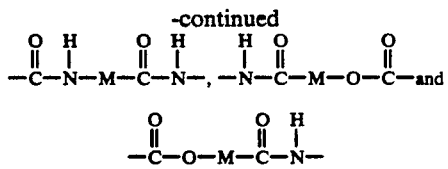

where M is a molecular moiety,
x and y may be the same or different and are between 1 and 6, $B_1$ and $B_2$ may be the same or different and are chosen from phenyl, alkylphenyl or any molecular moiety made hydrophobic by attachment of a group containing from 8 to 40 carbon atoms, P is selected from a $C_1$ to $C_6$ alkyl group,

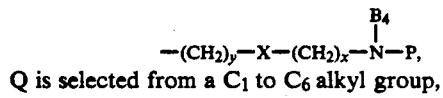

Q is selected from a $C_1$ to $C_6$ alkyl group,

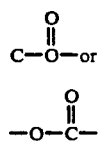

$-(CH_2)_y-X-M$ and $-(CH_2)_y-Z-M$ where Z is either where $B_3$ and $B_4$ may be the same or different from $B_1$ and $B_2$ and are chosen from the same list of substituent groups with the proviso that when the compound contains only 2 nitrogen atoms in the chain both $B_1$ and $B_2$ must be molecular moieties made hydrophobic by attachment of a group containing 8 to 40 carbon atoms and when the compound contains only 3 nitrogen atoms at least one of $B_1$, $B_2$, $B_3$ or $B_4$ must be a molecular moiety made hydrophobic by attachment of a group containing 8 to 40 carbon atoms in which alternating layers are provided, a first layer containing chromophore groups and the second layer not containing chromophore groups.

7. A method for the preparation of films from a material having the general formula

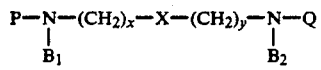

where X is selected from

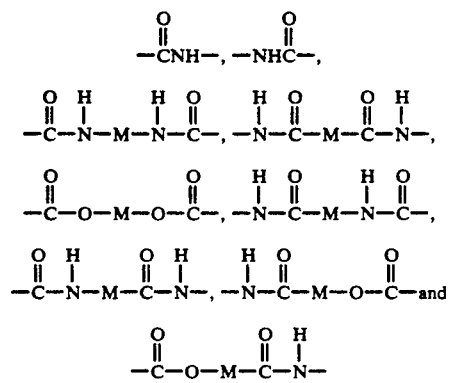

where M is a molecular moiety, x and y may be the same or different and are between 1 and 6, $B_1$ and $B_2$ may be the same or different and are chosen from phenyl, alkyl-phenyl or any molecular moiety made hydrophobic by attachment of a group containing from 8 to 40 carbon atoms, P is selected from a $C_1$ to $C_6$ alkyl group,

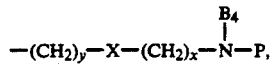

Q is selected from a $C_1$ to $C_6$ alkyl group,

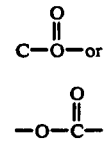

$-(CH_2)_y-X-M$ and $-(CH_2)_y-Z-M$ where Z is either where $B_3$ and $B_4$ may be the same or different from $B_1$ and $B_2$ and are chosen from the same list of substituent groups with the proviso that when the compound contains only 2 nitrogen atoms in the chain both $B_1$ and $B_2$ must be molecular moieties made hydrophobic by attachment of a group containing 8 to 40 carbon atoms and when the compound contains only 3 nitrogen atoms at least one of $B_1$, $B_2$, $B_3$ or $B_4$ must be a molecular moiety made hydrophobic by attachment of a group containing 8 to 40 carbon atoms comprising passing a surface of a substrate into a liquid on the surface of which is deposited a compressed mono-molecular layer of a first material of the invention and then successively out of or into at least one liquid provided with a compressed mono-molecular layer of a material according to the invention which may be the same or different from the first material.

8. A method according to claim 7 in which the substrate coated with the first material is passed through a second compressed mono-molecular layer which is different from the first material to provide a substrate carrying a non-centrosymmetric film.

9. An optical switching device comprising a substrate carrying a non-centrosymmetric film comprising a material having the general formula

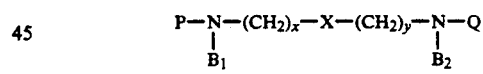

where X is selected from

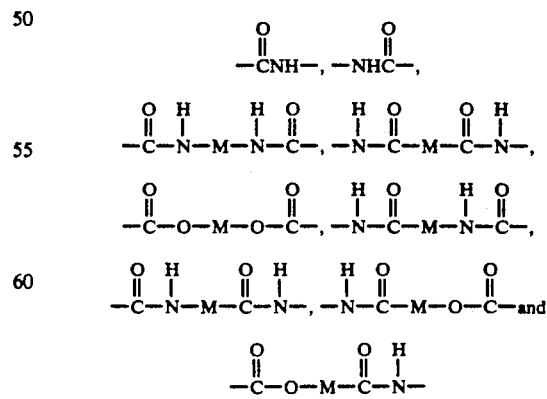

where M is a molecular moiety, x and y may be the same or different and are between 1 and 6, $B_1$ and $B_2$ may be the same or different and are chosen from phenyl, alkylphenyl or any molecular moiety made hydrophobic by attachment of a group containing from 8 to 40 carbon atoms, P is selected from a $C_1$ to $C_6$ alkyl group, $$-(CH_2)_y-X-(CH_2)_x-\overset{B_4}{\underset{|}{N}}-P,$$

Q is selected from a $C_1$ to $C_6$ alkyl group, $$\overset{O}{\underset{\|}{C}}-O- \text{ or}$$

$$-O-\overset{O}{\underset{\|}{C}}-$$

$-(CH_2)_y-X-M$ and $-(CH_2)_y-Z-M$ where Z is either where $B_3$ and $B_4$ may be the same or different from $B_1$ and $B_2$ and are chosen from the same list of substituent groups with the proviso that when the compound contains only 2 nitrogen atoms in the chain both $B_1$ and $B_2$ must be molecular moieties made hydrophobic by attachment of a group containing 8 to 40 carbon atoms and when the compound contains only 3 nitrogen atoms at least one of $B_1$, $B_2$, $B_3$ or $B_4$ must be a molecular moiety made hydrophobic by attachment of a group containing 8 to 40 carbon atoms.

* * * * *